United States Patent
Fernkvist et al.

(10) Patent No.: US 8,669,412 B2
(45) Date of Patent: Mar. 11, 2014

(54) METHOD AND ARRANGEMENT FOR MANUFACTURING A LAMINATED STRUCTURE

(75) Inventors: Maria Fernkvist, Molndal (SE);
Maryam Tondkar, Hisings Backa (SE)

(73) Assignee: SCA Hygiene Products AB, Göteborg (SE)

( * ) Notice: Subject to any disclaimer, the term of this patent is extended or adjusted under 35 U.S.C. 154(b) by 326 days.

(21) Appl. No.: 12/920,729

(22) PCT Filed: Apr. 18, 2008

(86) PCT No.: PCT/SE2008/050445
§ 371 (c)(1),
(2), (4) Date: Sep. 2, 2010

(87) PCT Pub. No.: WO2009/128757
PCT Pub. Date: Oct. 22, 2009

(65) Prior Publication Data
US 2011/0004178 A1  Jan. 6, 2011

(51) Int. Cl.
*A61F 13/15* (2006.01)
(52) U.S. Cl.
USPC ............................ 604/383; 604/365; 604/380
(58) Field of Classification Search
USPC ................... 604/365, 378, 380, 383
See application file for complete search history.

(56) References Cited

U.S. PATENT DOCUMENTS

| | | | |
|---|---|---|---|
| 4,761,322 A | 8/1988 | Raley | |
| 5,591,149 A | 1/1997 | Cree et al. | |
| 5,649,915 A | 7/1997 | Chauvette et al. | |
| 5,855,719 A * | 1/1999 | Menard | 156/256 |
| 5,876,388 A | 3/1999 | McDowall et al. | |
| 6,277,223 B1 * | 8/2001 | Herrin et al. | 156/73.1 |

(Continued)

FOREIGN PATENT DOCUMENTS

| | | |
|---|---|---|
| EP | 1 216 679 A2 | 6/2002 |
| JP | 61-141361 A | 6/1986 |

(Continued)

OTHER PUBLICATIONS

Translation of Office Action (Notice of Reasons for Rejection) dated Aug. 14, 2012, issued by the Japanese Patent Office in corresponding Japanese Patent Application No. 2011-504955 (4 pages).

(Continued)

*Primary Examiner* — Lynne Anderson
(74) *Attorney, Agent, or Firm* — Buchanan Ingersoll & Rooney PC (57) ABSTRACT

A method for manufacturing a laminated structure for use in an absorbent article such as a diaper, a sanitary napkin, a panty liner, an incontinence pad or similar and being defined by a plurality of material layers comprising at least a first layer which is liquid-permeable, a second layer constituting an absorbent core and a third layer, each of the layers being formed of a material having a certain pore radius. The method includes bonding together the material layers by means of at least two ultrasonic welding steps; and providing an ultrasonic welding pattern for each of the welding steps, each of the welding patterns being defined by a plurality of bonding sites. The method includes providing the welding steps for forming generally the entire absorbent article; and selecting the welding patterns in a manner so that at least the entire laminated structure has a multiple pore radius.

19 Claims, 4 Drawing Sheets

(56) References Cited

U.S. PATENT DOCUMENTS

| | | |
|---|---|---|
| 6,350,711 B1 | 2/2002 | Potts et al. |
| 6,414,216 B1 | 7/2002 | Malowaniec |
| 6,462,253 B1 | 10/2002 | Magnusson et al. |
| 6,526,631 B1 | 3/2003 | Alberg et al. |
| 6,878,857 B1 | 4/2005 | Chihani et al. |
| 2003/0093044 A1 | 5/2003 | Wahlstrom et al. |
| 2004/0254552 A1 | 12/2004 | Mangold |
| 2007/0034315 A1* | 2/2007 | Sandin et al. ............... 156/73.1 |
| 2009/0204093 A1* | 8/2009 | Vasic et al. ............... 604/385.23 |

FOREIGN PATENT DOCUMENTS

| | | |
|---|---|---|
| JP | 2000-024033 A | 1/2000 |
| JP | 2002-516715 A | 6/2002 |
| JP | 2003-527929 A | 9/2003 |
| JP | 2004-049405 A | 2/2004 |
| RU | 2 104 037 C1 | 2/1998 |
| RU | 2 228 161 C2 | 5/2004 |
| RU | 2 255 721 C2 | 7/2005 |
| WO | WO 99/49825 A1 | 10/1999 |
| WO | 99/62446 A1 | 12/1999 |
| WO | WO 00/02727 A1 | 1/2000 |
| WO | 01/72254 A2 | 10/2001 |
| WO | 2005120412 | 12/2005 |
| WO | WO 2007/069967 A1 | 6/2007 |
| WO | 2009105000 | 8/2009 |

OTHER PUBLICATIONS

Office Action (Decision on Grant) dated Apr. 19, 2012, issued in corresponding Russian Patent Application No. 2010146930, and an English Translation thereof. (5 pages).

International Search Report (PCT/ISA/210) for PCT/SE2008/050445 dated Dec. 15, 2008.

Office Action issued on Dec. 18, 2012 in corresponding Colombian Patent Application No. 10142935, and an English language summary thereof.

Search Report issued in corresponding European Patent Application No. 08779246.1, dated Jul. 9, 2013.

* cited by examiner

METHOD AND ARRANGEMENT FOR MANUFACTURING A LAMINATED STRUCTURE

TECHNICAL FIELD

The present invention relates to a method for manufacturing a laminated structure for use in an absorbent article such as a diaper, a sanitary napkin, a panty liner, an incontinence pad or similar and being defined by a plurality of material layers comprising at least a first layer which is liquid-permeable, a second layer constituting an absorbent core and a third layer, each of said layers being formed of a material having a certain pore radius, said method comprising: bonding together said material layers by means of at least two ultrasonic welding steps; and providing an ultrasonic welding pattern for each of said welding steps, each of said welding patterns being defined by a plurality of bonding sites.

The present invention also relates to an arrangement for manufacturing a laminated structure for use in an absorbent article such as a diaper, a sanitary napkin, a panty liner, an incontinence pad or similar and being defined by a plurality of material layers comprising at least a first layer which is liquid-permeable, a second layer constituting an absorbent core and a third layer, each of said layers being formed of a material having a certain pore radius, said arrangement comprising: at least two ultrasonic welding devices for bonding together said material layers; each of said ultrasonic welding devices being arranged for providing an ultrasonic welding pattern being defined by a plurality of bonding sites.

The present invention also relates to a laminated structure for use in an absorbent article such as a diaper, a sanitary napkin, a panty liner, an incontinence pad or similar and being defined by a plurality of material layers comprising at least a first layer which is liquid-permeable, a second layer constituting an absorbent core and a third layer, each of said layers being formed of a material having a certain pore radius, said laminated structure being formed by bonding together said material layers by means of at least two ultrasonic welding steps providing an ultrasonic welding pattern for each of said welding steps, each of said welding patterns being defined by a plurality of bonding sites.

STATE OF THE ART

Today's absorbent articles, such as diapers, panty liners, incontinence pads, training pants and similar articles, are normally manufactured by means of methods and systems in which different types of material layers and absorbent bodies are combined.

A conventional absorbent article is normally designed as a layered product comprising a liquid-permeable top sheet (for example a nonwoven material based on synthetic or natural fibres) that faces the wearer's body, an absorbent structure (for example a fibrous material layer serving as a liquid-distributing or liquid-transferring layer and an absorbent core) and a liquid-impermeable bottom layer, for example in the form of a thermoplastic backsheet that faces the wearer's clothing. These different layers can be in the form of single material sheets or laminated structures.

It is previously known to manufacture various types of laminates of different material layers, for example different fibrous layers, for use as an absorbent article of the above-mentioned type. A manufacturing process for such articles normally comprises different process steps wherein the layers in the laminate structure are bonded to each other by means of different types of technology, for example gluing, heat bonding or ultrasonic bonding.

A gluing process is based on applying adhesive on a material layer, according to a predetermined gluing pattern, and then bonding the material layer onto a further material layer. Furthermore, in a heat bonding process, two or more layers in the laminate are attached by heat melting fibres in a layer having heat-meltable fibres. To this end, the layers are fed through an arrangement having a nip which is defined by two rolls being designed with a particular bonding pattern. Finally, an ultrasonic bonding process comprises feeding two or more material layers between a ultrasonic horn and a further roll (normally a so-called pattern roll) so that they are bonded together with a certain bonding pattern. All these above-mentioned technologies are well-known to the skilled person and are used for producing laminate structures for absorbent articles.

With regard to today's technology, there is a continuous demand for improvements of certain characteristics of absorbent articles. For example, it is important that such an article has optimum fluid absorption properties so that a high degree of acquisition of fluid is achieved. Also, the article must be designed with a low degree of rewetting and it must also be perceived by the wearer as being dry during use. This means that the article must have improved fluid diffusion properties in order to provide better comfort for the user.

Regarding prior art, it can be noted that the document WO 00/02727 teaches a system and a method for producing a material laminate by ultrasonically welding pieces of material on an advancing material web. The system shown in WO 00/02727 comprises a first ultrasonic welding station in which said pieces of material are attached by means of a first ultrasonic horn, and a second ultrasonic welding station in which the pieces of material are subsequently fixed onto the material web by means of a second ultrasonic horn.

Furthermore, the patent document EP 1216679 discloses a method for producing a laminate of fibrous material layers by bonding the material layers together using ultrasonic welding. In particular, EP 1216679 teaches a method comprising two steps, i.e. a first step in which two layers are ultrasonically bonded together in a first bonding pattern followed by a second step in which the two interconnected layers are ultrasonically bonded to a third layer. The second bonding pattern is different from the first pattern in such a way that is has a different bonding area.

There is also disclosed in EP 1216679 how the bonding pattern affects the properties of the laminate with regard to the stiffness and stability of a belt in belted diapers and incontinence protection articles.

DISCLOSURE OF THE INVENTION

An object of the present invention is to provide a method and arrangement for producing a material laminate for an absorbent article, in particular for providing an absorbent article which is improved with regard to prior art and which has optimum fluid absorption properties and a relatively low degree of rewetting, and which also is perceived by a user as being dry during use.

This object is accomplished by means of a method of the kind mentioned initially, said method comprising providing said welding steps for forming generally the entire absorbent article; and selecting said welding patterns in a manner so that at least the entire laminated structure has a multiple pore radius.

The object of the invention is also accomplished by means of an arrangement of the kind mentioned initially, wherein the ultrasonic welding devices are arranged for providing said welding steps for forming the entire absorbent article, wherein said welding patterns are selected in a manner so that at least the entire laminated structure has a multiple pore radius.

The object of the invention is also accomplished by means of a laminated structure as initially mentioned, which is formed through said welding steps wherein generally the entire absorbent article is formed; and wherein said welding patterns are selected in a manner so that at least the entire laminated structure has a multiple pore radius.

By means of the invention, certain advantages are obtained. Firstly, it can be noted that by welding the layers together in several steps it would be possible to obtain a product having different bonding patterns between the layers. A product having such a structure would provide better drainage and diffusion properties due to a multiple pore radius.

By means of the invention, an improved contact between the materials is also provided, as well as a smoother structure of the article, which means that an improved comfort for the user of the article can be achieved.

In contrast to prior art, the invention provides a solution to the above-mentioned problem due to the fact that it relies on the insight that the above-mentioned ultrasonic welding steps influence properties such as the drainage and absorption of fluid in an absorbent product.

According to an embodiment, the invention is preferably arranged so that generally the entire article is formed by bonding together the material layers in a manner comprising a first welding step in which the third layer and the second layer are bonded together, and a second welding step in which the bonded third and second layers are bonded together with said first layer.

Also, according to an embodiment, the invention is preferably arranged so that the first layer is formed from a material having a pore radius which is equal to or greater than the pore radius of the second layer and the third layer, and also so that the second layer is formed from a material having a pore radius which is equal to or greater than the pore radius of the third layer. This contributes to providing an absorbent article which has improved properties—as compared with prior art—with regard to the fluid absorption, rewetting and dryness.

BRIEF DESCRIPTION OF DRAWINGS:

The invention will now be described with reference to a preferred embodiment and the appended drawings, wherein.

PREFERRED EMBODIMENT

The principles of the present invention will now be described with reference to an embodiment of the invention. More precisely, the invention is suitably used in connection with absorbent articles, for example in the form of a thin sanitary napkin. However, the invention is not limited to such absorbent articles only, but can in principle also be used for manufacturing diapers, panty liners, incontinence pads, training pants and similar articles.

The invention is intended for use during manufacturing of such absorbent articles. More precisely, the invention is generally used for joining two or more material layers, normally fibrous layers, forming part of the finished absorbent article.

Figure 1:
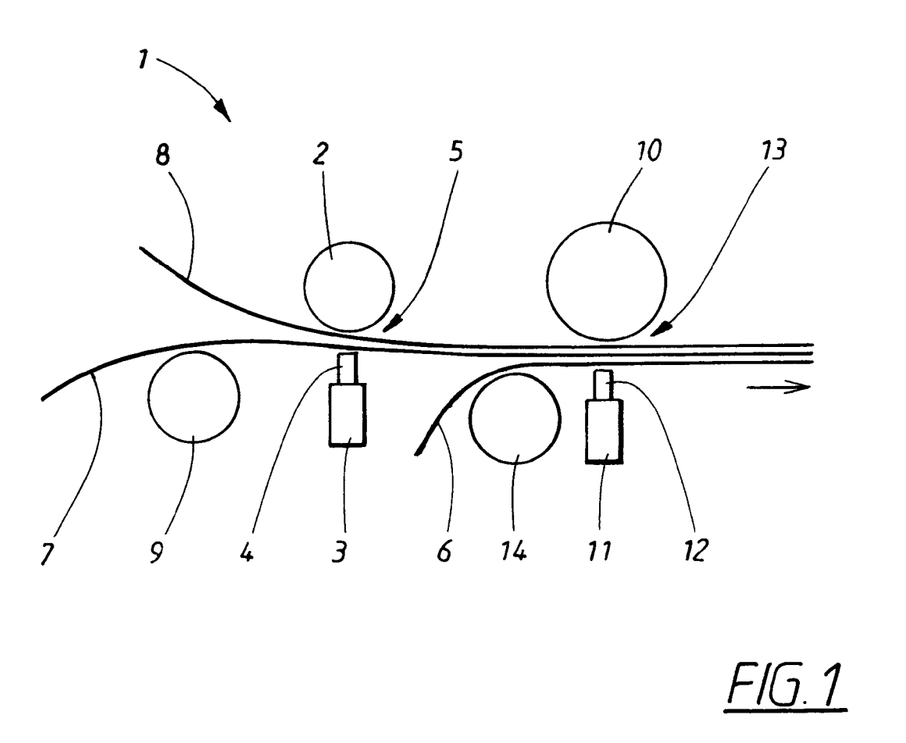
FIG. 1 is a schematical view of an arrangement for manufacturing absorbent bodies in accordance with the principles of the present invention.

FIG. 1 shows an arrangement 1 for producing such a laminate of a plurality of material layers. The arrangement comprises a first roll 2 and an ultrasonic welding device 3 having an ultrasonic horn 4. The horn 4 is positioned at a predetermined, relatively small distance from the roll 2, thereby defining a gap 5 through which certain material layers are to be fed. According to a suitable embodiment, the invention is arranged for binding together a first layer 6, a second layer 7 and a third layer 8. Also, according to an embodiment, the first layer 6 is a liquid-permeable topsheet, the second layer 7 is an absorbent body and the third layer 8 is a liquid-impermeable backsheet. However, as will be explained below, the invention is not limited to such configuration only, but can be varied in accordance with the appended claims.

As shown in FIG. 1, the second material layer 7 is suitably guided along a second roll 9. According to the embodiment, the invention is arranged for operating in a series of process steps. The first of such process steps is a step for binding together the third layer 8 and the second layer 7. After this step, the laminate being formed by the third material layer 8 and the second material layer 7 is joined together with the first layer 6.

According to previously known principles, the first roll 2 is formed with a pattern (not shown) in the form of a particular surface structure on its outer surface. The purpose of this pattern is to aid in binding together the third material layer 8 and the second material layer 7 during operation of the ultrasonic horn 4. Properties such as the design, dimensions and depth of this pattern are defined on the basis of requirements relating to the desired design and appearance of the final laminate. The pattern on the first roll 2 may suitably comprises recessed parts and raised parts, wherein the raised parts constitute binding points, i.e. bonding sites, when the third layer 8 and the second layer 7 are fastened onto each other. The depth of the pattern is preferably in the magnitude of approximately 0.3-2 mm.

The manner in which the ultrasonic welding device 3 can be used is previously known as such and for this reason it will not be described in greater detail here. However, it can be noted that ultrasonic welding devices in general can be used for welding, cutting, perforation or other types of material treatment. In the context of the present invention, it is assumed that the treatment in question is ultrasonic welding, for the purpose of bonding together two or more material layers of an absorbent product in order to improve the drainage and diffusion properties of the absorbent product. The invention is arranged in particular to use ultrasonic welding in order to modify or adapt the pore structure of the layers 6, 7, 8 forming part of the product. In particular, the invention is arranged for welding together generally the entire absorbent article in order to change the pore structure.

The second and third material layers 7, 8 shown in FIG. 1 are fed through the gap 5 to be bonded together by means of a given bonding pattern provided on the first roll 2 as mentioned above. The bonding pattern is chosen in accordance with requirements regarding the visual appearance, i.e. the design, of the finished product, and also in accordance with requirements regarding the bonding strength between the two material layers 7, 8 and other requirements of the finished article.

When the second and third material layers 7, 8 have been bonded together to form a laminate, they are fed towards a further, third roll 10 and a second ultrasonic welding device 11 having an ultrasonic horn 12. In a manner which corresponds to the first gap 5, a second gap 13 is defined between the third roll 9 and the second ultrasonic horn 11. The second and third material layers 7, 8 are laminated to the first material layer 6 which is also fed through the second gap 13. To this end, the first material layer 6 is suitably guided along a fourth roll 14. The material layers 6, 7, 8 are fed in a direction which is indicated by means of an arrow in FIG. 1.

The bonding operation at the second ultrasonic welding device 11 is carried out with a further bonding pattern, which may or may not be similar to the first bonding pattern provided by the first ultrasonic welding device 3. The same principles regarding the design and possible dimensions which have been described with reference to the first ultrasonic welding device 3 also apply to the second ultrasonic welding device 11.

The two above-mentioned welding steps for bonding the three material layers 6, 7, 8 are arranged so as to give the finished absorbent article a desired design and a certain strength. It should be noted that the strength of the article is given primarily due to the fact that the structure becomes more stable due to the welding process and furthermore due to the fact that the welding process leads to a relatively bulky structure which provides an improved comfort. Other properties such as the degree of fluid acquisition, the dryness and the diffusion of fluid are determined at least partly by means of the two welding steps as described.

The combined laminate comprising the three material layers 6, 7, 8 is suitably used for manufacturing an absorbent article. As an example only, it can be assumed that the first layer 6 is a liquid-permeable topsheet, suitably a nonwoven material based on synthetic or natural fibres, which is arranged to be closest to the body of the wearer of the finished article during use thereof. According to such an example, the first layer 6 is suitably manufactured from a nonwoven material being constituted by synthetic fibres such as polyethene, polypropylene, polyester, nylon or similar. Other fibres such as for example binding fibres, copolymer fibres, split fibres, nanofibres etc. can also be used. Also, mixtures of different fibre types can be used for this purpose. Alternatively, the first layer 6 can be made of other materials, such as a thermoplastic film or a polyester film, or a laminate or a combination of different laminates. It can also be perforated or non-perforated, in accordance with a predetermined pattern.

Regarding the first material layer 6, it can be furthermore be noted that the invention is suitably implemented in a manner so that the first material 6 is of a kind which has the largest pores of the different layers 6, 7, 8 in the laminate. The largest pores are relatively easy to drain, meaning that liquid being held within the pore structure of the first material layer 6 can be relatively easily drained into the adjacent material layer, i.e. the second material layer 7. This feature is based on the insight that the pores which are relatively large are easy to empty. A purpose of the invention is thus to empty the pores of the first material of fluid generally immediately.

In other words, the first material layer 6 is preferably chosen so that it has larger pores than the remaining layers 7, 8 in order to provide efficient drainage of fluid. Also, the limitations and dimensions of the magnitude of the pores of the first layer 6 are primarily related to the lower layers 7, 8. These principles will be described in greater detail below, with reference to FIGS. 3-5.

Furthermore, the first layer 6 is preferably designed with dimensions chosen such that its maximum thickness is preferably of the magnitude 5 mm and its maximum basis weight is preferably approximately 100 $g/m^2$, most preferably 50 $g/m^2$. Furthermore, the first layer 6 can itself be in the form of a laminate having different types of fibre structure. However, the total basis weight should preferably not exceed 100 $g/m^2$.

Furthermore, and also according to the embodiment shown in FIG. 1, the second layer 7 can be in the form of an absorbent structure or layer, or absorbent core, suitably comprising a fibrous material, which is designed for having a suitable degree of acquisition, diffusion and absorption of fluid. For this reason, the second layer 7 can be a porous, elastic, relatively thick material layer, for example in the form of a fibrous wadding material or a similar type of material with a high degree of intake of fluid and a high degree of absorption of fluid.

The second layer 7 can comprise natural or synthetic fibres, or a mixture of such fibres. Furthermore, the second layer 7 may comprise a suitable amount of a superabsorbent material. Such an arrangement will contribute to a very high absorption rate of the complete absorbent article. Furthermore, the second layer 7 can be a single material layer or a laminate. In the latter case, the second layer 7 may be constituted by a laminate with a wadding layer and an absorbent core.

It can also be mentioned that the second layer 7 may comprise a suitable amount of thermoplastic fibres in order to allow an ultrasonic welding process in a proper manner.

Furthermore, in accordance with the principles of the invention, the second layer 7 is preferably designed with a pore structure which is finer than the first layer 6, i.e. having less pore radius than the first layer 6. Also, the pore radius of the second layer 7 should be greater than the pore radius of the third layer 8, i.e. the second layer 7 has a more coarse fibre structure than the third layer 8 (and any further lower layers).

Finally, according to the embodiment, the third layer 8 can be a backsheet layer which is preferably liquid-impermeable (or has at least a very high resistance against penetration of liquid) and is consequently provided in order to prevent leakage of fluid out from the finished article. To this end, the third layer 8 is suitably manufactured from a liquid-impermeable material such as a thin and sealing plastic film. For example, plastic films made from polyethene, polypropylene or polyester can be used for this purpose.

According to an alternative embodiment, the third material layer 8 can be of different type than the above-mentioned backsheet, for example a further absorbent layer.

Figure 2A:
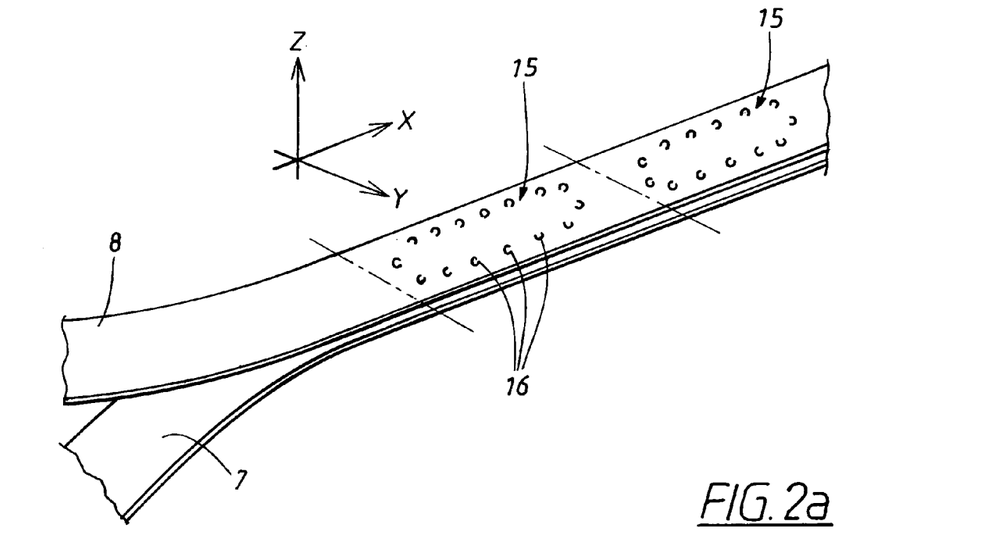
FIG. 2a is a schematic perspective view showing a first bonding step in accordance with the invention.

Furthermore, FIG. 2a shows a simplified perspective view of a bonding process for the third material layer 8 and the second material layer 7, in accordance with a suitable embodiment of the invention. The drawing shows a first bonding pattern 15 being produced as a result of the second and third layers 7, 8 being guided past the first ultrasonic welding device 4 and being bonded together. The actual design of the first bonding pattern 15 is chosen with regard, for example, to the visual appearance of the article, the strength of the finished article and the fluid acquisition properties. The actual design of the bonding pattern 15 may vary. For example, the bonding pattern 15 can be in the form of a square or rectangular pattern having a distance of 1-3 cm between bonding sites. Preferably, the distance between the bonding site of the bonding pattern 15 should not exceed approximately 3 cm, in order to provide an efficient drainage of the article.

FIG. 2a also indicates a coordinate system according to which the material layers 8, 7 are arranged in accordance with the invention. More precisely, the longitudinal direction along which the material layers 8, 7 extend is referred to as the x direction. The direction transverse to the x direction is referred to as the y direction, and the direction perpendicular to the plane generally defined by the surface of each of the material layers 8, 7 is referred to as the z direction.

After the third and second layers 8, 7 have been bonded together, they are further bonded to the first layer 6 in a similar manner by means of the second ultrasonic horn 11. This is shown in a schematical manner in FIG. 2b. In this manner, a second bonding pattern 17 is defined, also comprising a plurality of bonding sites 18. According to the embodiment, the first bonding pattern 15 and the second bonding pattern 17 are different from each other, but they may have similar form also.

Figure 2B:
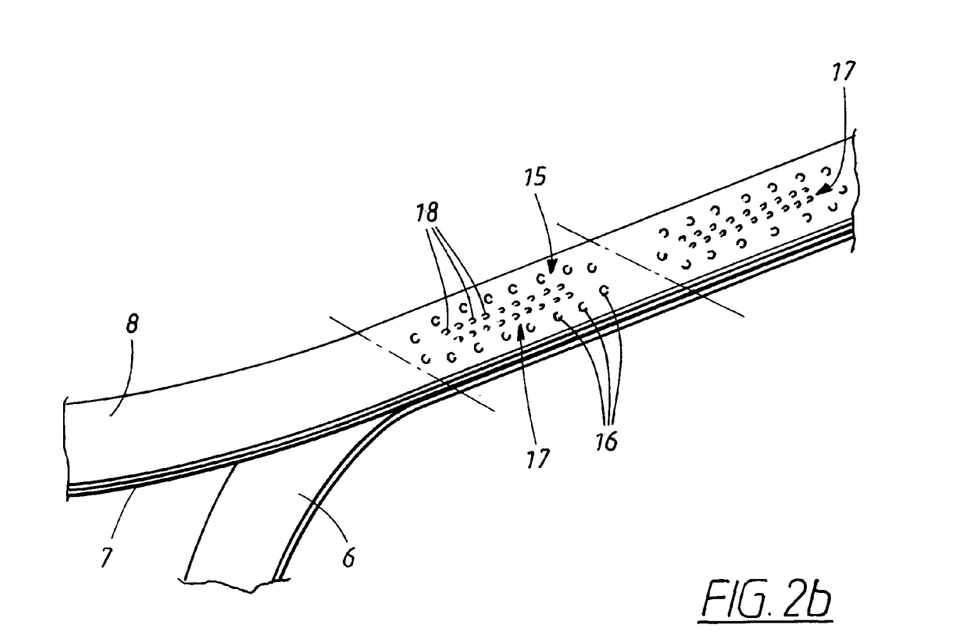
FIG. 2b is a schematic perspective view showing a second bonding step in accordance with the invention.

The order of welding together the layers 6, 7, 8 is consequently illustrated by means of FIGS. 2a and 2b. An important feature of the invention is in fact that the welding is carried out in a particular order, i.e. first the third material layer 8 (suitably a backsheet) and the second material layer 7 (suitably an absorbent layer). When these two layers 7, 8 have been bonded, the first layer 6 (suitably a topsheet) is suitably added to the other layers by bonding also.

Consequently, in order to provide a laminate in accordance with the principles of the invention, it is consequently preferable to start this process by welding the second and third layers 7, 8, i.e. those layers which are furthest away from the body during use of the absorbent product. The reason for this is that (i.e., if one starts with the upper, first layer 6) there is a risk that the pores are too small and as a consequence, the first layer 6 becomes too dense and impermeable. This is contrary to the purpose of the invention. It will consequently be impossible to create a finer fibre structure (i.e. having smaller pores) when it is welded to the remaining layers. In such a case, an efficient drainage will be impossible.

A further important principle is that the welding is suitably to be carried out between all the material layers 6, 7, 8 which form the finished product, i.e. including the second layer 7 which in this case is an absorbent layer.

Figure 3:
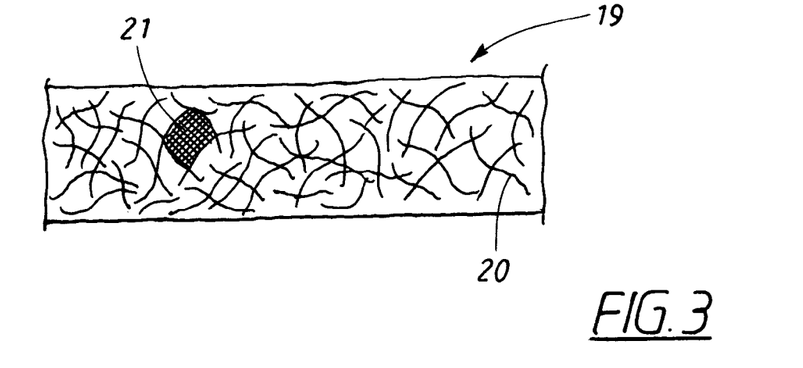
FIG. 3 is a schematical drawing illustrating the principles of the pore radius of an absorbent body.

In order to further explain the principles and features of the invention, a few basic concepts will now be described. Firstly, the term "pore radius" as mentioned above will now be described with reference to FIG. 3 which shows a cross-section of an absorbent layer 19 with a mesh 20 or matrix being formed of fibrous material. The fibrous mesh 20 defines a plurality of pores, each having a certain size and volume. As an example, a certain pore is schematically referred to by means of reference numeral 21 in FIG. 3. For this pore 21 (and for any pore in the mesh 20), a measure of its "pore radius" can be determined. Due to the irregular form of the fibrous mesh 20, these pores are obviously not perfectly circular. Instead, a measure of the "effective" pore radius R of a pore can be obtained by means of the Laplace equation. This is previously known as such and for this reason it will not be described in detail here. It can just be mentioned that the effective pore radius R is an approximation according to the following relationship:

$$R = 2\gamma_L \cos\theta_{a,r}/\Delta_p$$

where $\gamma_L$ is the surface tension of the liquid, $\theta_{a,r}$ is the advancing or receding contact angle of the liquid with reference to the structure and $\Delta_p$ is the pressure difference across the meniscus defining the surface of the liquid toward the air.

Figure 4:
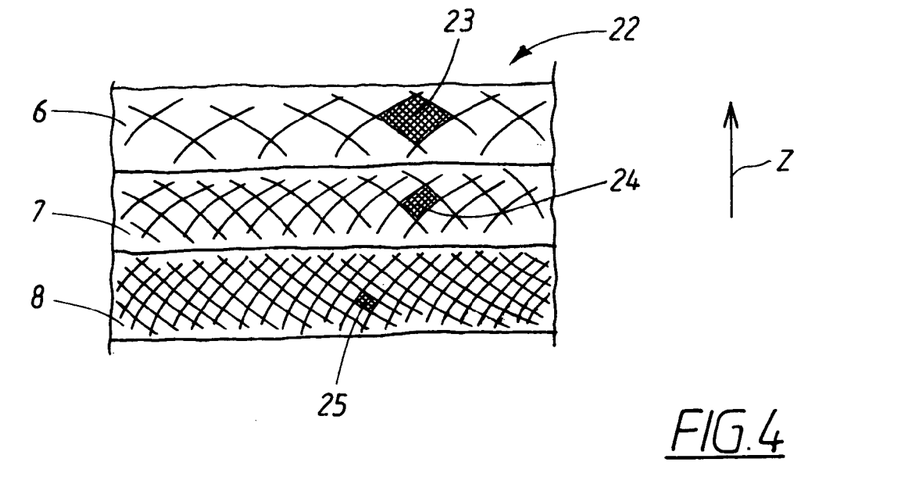
FIG. 4 is a schematical drawing illustrating the principles of the pore gradient of a laminated structure formed in accordance with the principles of the present invention.

The principles of the invention will further be described with reference to FIG. 4, which shows a laminated structure (also referred to as a laminate) 22 being composed of three different fibrous layers corresponding to the three material layers 6, 7, 8 of the present invention. Examples of three different pores 23, 24, 25, one in each layer 6, 7, 8, are indicated in the drawing. As indicated above, the invention is arranged so that the first layer 6 is formed from a material wherein its corresponding pore 23 has a pore radius R1 which is equal to or greater than the pore radius R2 of the corresponding pore 24 of the second layer 7 and the pore radius R3 of the corresponding pore 25 of third layer 8. Also, the second layer 7 is of a material which has a pore radius R2 which is equal to or greater than the pore radius R3 of the third layer 8. This means that the laminate has a pore gradient which varies in the z direction (cf. FIG. 2a) due to the diminishing sizes of the pore radius as regarded from the first material layer 6 toward the third material layer 8.

As an example, it could be mentioned that a laminate (not shown in the drawings) having material layers each defining a pore radius of a particular magnitude so that R1<R2>R3 would not function in a manner as defined by the invention. In particular, such a solution would not provide the intended drainage effect since the fluid would not be drawn in an efficient manner from the top layer toward the middle layer.

According to the embodiment, the laminate is consequently produced in a manner so that it has a pore gradient in a direction through the finished laminate (the "z direction"), i.e. so that the topside of the finished article has a relatively "loose" and "open" pore structure, and so that the rear side of the article has a more "dense" and "closed" pore structure.

As an alternative to the embodiment described above, in which the first material layer 6 has pores of other dimensions than the second material layer 7 and the third material layer 8, it should be noted that the invention could also be implemented in a manner so that all the material layers 6, 7, 8 comprise pores of generally the same dimensions. The first mentioned case is based on the principle that a multiple pore gradient is obtained according to the invention with the use of layers 6, 7, 8 having different pore dimensions but using generally identical welding patterns in the two welding steps described above. The second case, on the other hand, is based on the principle that a multiple pore gradient is obtained through the used of two different welding patterns but with material layers having generally the same pore dimensions. Both these alternative solutions are possible to obtain within the scope of the present invention.

Figure 5:
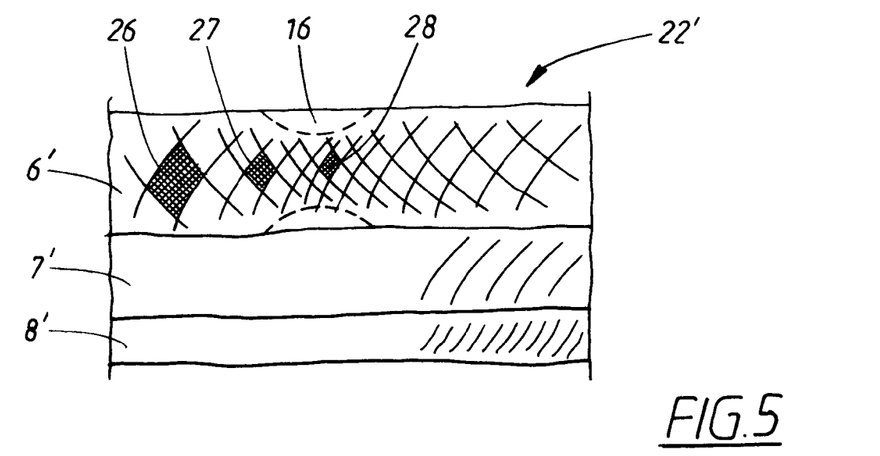
FIG. 5 is a schematical drawing illustrating the principles of a multiple pore radius of a laminated structure.

Furthermore, FIG. 5 is a schematical cross-sectional drawing of a laminate 22' according to a further embodiment of the invention. The laminate 22' comprises three material layers 6', 7', 8' each having a particular pore radius, wherein the pore radius of at least the first layer 6' varies in the x and y directions. This means that this first layer 6' is formed with a material having different fibrous structures along its longitudinal direction, i.e. the x direction. Furthermore, each of these structures has a different pore radius. This is shown schematically in FIG. 5, which shows that the first layer 6' has three different pores 26, 27, 28 with different pore radius.

As a result of the welding operation, the pores of the material layers 6', 7', 8' shown in FIG. 5 will be smaller and more dense in the vicinity of the bonding sites 16. Also, it can be noted that a pore gradient in the x and y directions is obtained around such bonding sites 16 as a result of the welding.

Consequently, the invention is preferably arranged so that the laminated structure is given a pore gradient both in the z direction and also in the x and y directions.

The actual ultrasonic welding process is based on the principle that the second and third layers 7, 8 are bonded to each other via the first bonding pattern 15 (cf. FIG. 2*a*), which comprises a plurality of bonding sites 16 which are formed by compressing these material layers 7, 8 (when passing through the gap 5) and by supplying a suitable amount of energy by means of the ultrasonic horn 4. This causes the material of the layers 7, 8 to soften and melt at the positions being defined by the bonding sites 16 so as to bond together.

The bonding patterns 15, 17 which are used in each bonding step are chosen so as to obtain better drainage and diffusion properties. According to the invention, improved drainage and diffusion properties for the finished article, and an improved contact between the material layers, are in particular obtained by choosing the bonding patterns 15, 17 in a manner so that the finished absorbent article is provided with multiple pore radius. This also has the advantage of a more dry surface of the article as well as an improved comfort.

This means that, according to the invention, the pore radius can be controlled so that, for example, the bonding sites 16 of the first bonding pattern 15 are chosen with a first predetermined pore radius and that the bonding sites 18 of the second bonding pattern 17 are chosen with a second predetermined pore radius, which is different from the pore radius of the first bonding pattern 15.

The pore gradient of an absorbent article affects the introduction of liquid to be transported into the underlying layers. According to the embodiment, the pore gradient are preferably controlled by arranging the pores of the different layers so that they are more and more "dense" for each layer or for each welding operation step. The invention is based on the principle that all the material layers 6, 7, 8 are bonded using ultrasonic welding, wherein the bonding patterns 15, 17 are chosen so that the pore gradient is optimized for each bonding operation.

Figure 6:
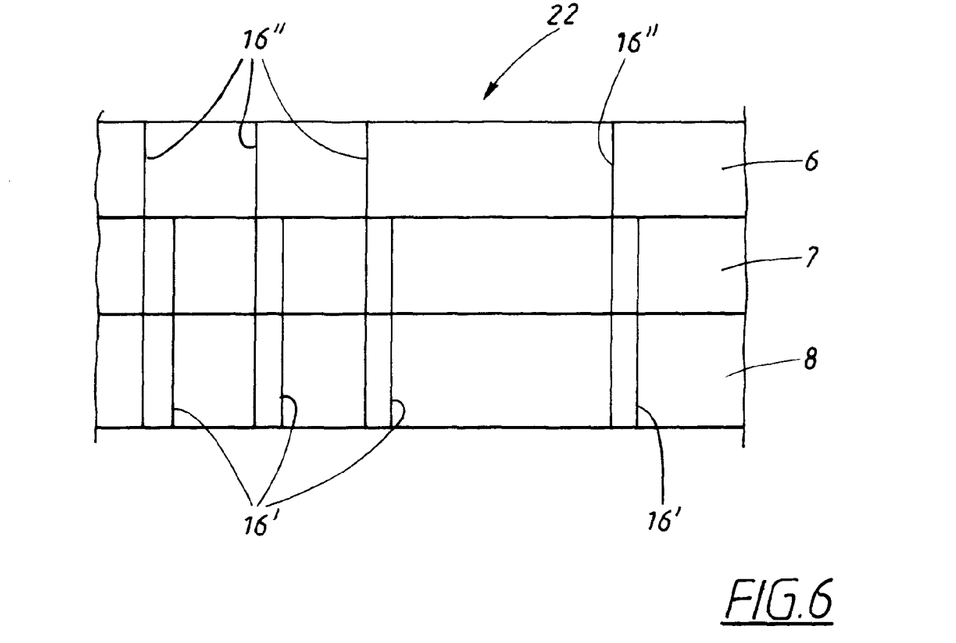
FIG. 6 is a schematical drawing which further explains the principles relating to a process for welding the laminated structure according to the invention.

FIG. 6 is a schematical cross-sectional view further showing the principles for welding a laminated structure 22 in accordance with the invention. The drawing corresponds generally to FIG. 4 but shows in particular the manner in which the three material layers 6, 7, 8 are provided with a particular welding pattern. More precisely, the second material layer 7 and the third material layer 8 are bonded by means of a first welding pattern, indicated in FIG. 6 as a number of bonding sites 16'. Furthermore, when the second and third layers 7, 8 are bonded and form a laminate, the first material layer 6 is bonded to this laminate by means of a second welding pattern, indicated in FIG. 6 as a number of further bonding sites 16".

The result of the welding operation shown in FIG. 6 is that the complete welding pattern will be the result of the bonding sites 16' connecting the second and third layers 7, 8 and also the further bonding sites 16" connecting all the layers 6, 7, 8. This means that there will be more welding sites between the second and third layers 7, 8 than between the first and second layers 6, 7. In this manner, the pore gradient of the laminated structure 22 can be controlled by means of the welding operation.

In the context of the present invention, optimizing the pore gradient means affecting the drainage, diffusion and dryness of the finished article in an improved manner.

For example, the invention can be implemented in a manner wherein the material is more open towards the rear (bottom) part of the article than the surface part, in order to obtain an article in which a high degree of fluid diffusion is obtained and so that the fluid is transported quickly away from the surface of the article. Here, it should be noted that it is important to achieve a close contact between the material layers 6, 7, 8. This is possible with the ultrasonic welding steps as explained above.

The invention also provides an improved and more soft material structure through the fact that the above-mentioned welding steps create a somewhat "bulky" structure. This means that the upper layer is formed with "crests" or "ridges" which have a tendency to create an increased volume between the user's body and the surface of the upper layer. Consequently, a column or slit of air is created between the user and the article, which contributes to the efficiency of the input of fluid. It also contributes to an improved comfort since the fluid is more quickly drawn into the product and since it can be avoided that a film or coating of liquid is created between the user's body and the absorbent article.

Figure 7:
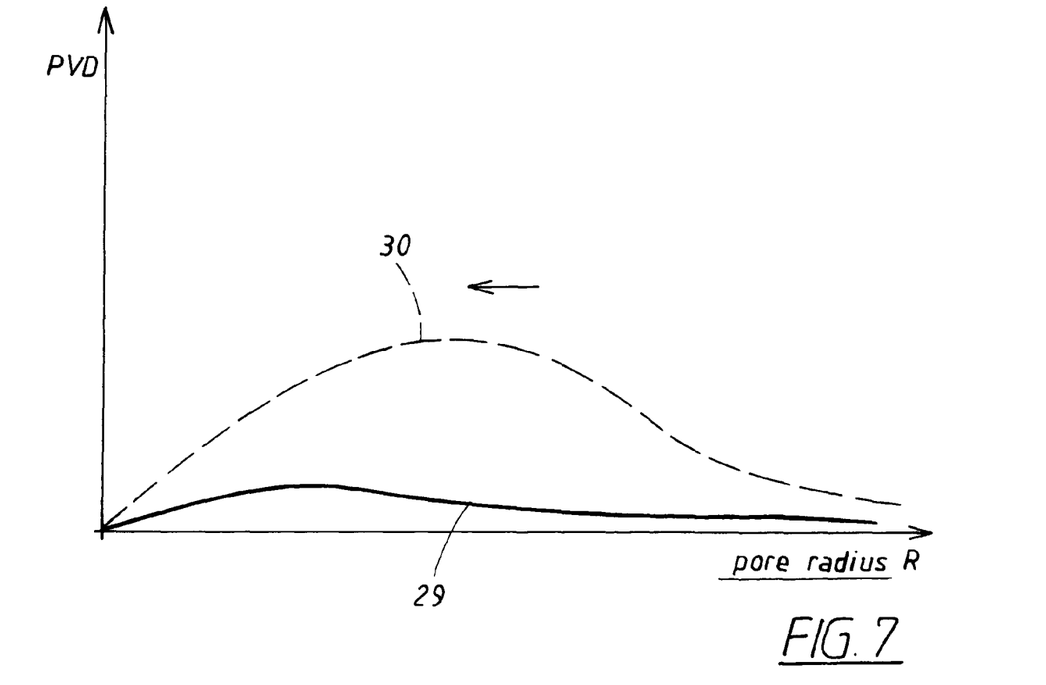
FIG. 7 is a diagram illustrating the principles of the invention.

The invention is based on the principle that the use of different bonding patterns will provide a product having multiple pore radius. FIG. 7 is a diagram showing two graphs which illustrate the purpose and function of the invention according to this principle.

The first graph 29, illustrated in the form of a continuous line, teaches how the pore volume distribution of a conventional laminated structure, i.e. a laminated structure which is not welded in a manner as defined by the invention, for an absorbent article varies with the pore radius. The second graph 30, illustrated with a broken line, teaches a corresponding situation but with a laminated structure which is welded and otherwise arranged in accordance with the present invention.

According to the graphs, it can be noted that the laminate according to the invention has a lower pore volume distribution (for a given pore radius) than the previously known material. This means that the material according to the invention has a higher degree of drainage than previous articles, which is an advantage since it gives the user an improved perception of dryness.

Furthermore, the first graph 29 teaches that the invention provides a pore volume distribution of the laminate which is generally independent of the pore radius. In contrast to this, the laminated structure according to the invention, as described by the second graph 30, has a pore volume distribution which is highly dependent of the pore radius. In particular, the second graph 30 has a "peak" corresponding to a pore radius of a predetermined magnitude, meaning that such a pore radius corresponds to a relatively high amount of fluid being collected in the surface part of the article.

According to the invention, an improved drainage of the article can be obtained by displacing the "peak" of the second graph 30 towards the left as regarded in the drawing. More precisely, the invention is arranged to displace this graph 30 towards the left for each welding step being carried out. This can be explained through the fact that a higher pressure is created in the pores due to the decreasing pore radius R. This means that more fluid will be released from the structure. This "displacement" of the second graph 30 towards the left is illustrated in a schematical manner by means of an arrow in FIG. 7.

Furthermore, due to the fact that the first layer 6, which closest to the user's body, has a pore radius which is equal to or greater than the pore radius of the second layer 7 and the third layer 8, and also that the second layer 7 has a pore radius which is equal to or greater than the pore radius of the third layer 8, an improved drainage is obtained by means of the invention.

The invention is not limited to the embodiment described above but can be varied within the scope of the appended claims. For example, the invention is not limited to any particular type of absorbent article, but can be used for manufacturing diapers, panty liners, incontinence pads, training pants and generally any other type of absorbent articles. Furthermore, the invention can be implemented using many types of materials and material combinations.

The basic concept of the invention has been described with reference to an embodiment with three different layers. However, the invention can alternatively be implemented with a different number of layers and a different number of ultrasonic welding steps, and also with different types of layers than those described above. For example, the invention can be implemented in a structure having two nonwoven layers and two absorbent cores. Alternatively, the invention can be implemented in a structure having a nonwoven layer, two absorbent cores and a backsheet. Generally, the invention is implemented in a manner wherein a number of layers form a laminated structure and wherein the welding patterns which are used preferably are selected so that generally the entire laminated structure is given a multiple pore radius.

Also, the ultrasonic welding of the different layers could either be done in one and the same step or in a number of consecutive steps.

The invention claimed is:

1. A method for manufacturing a laminated structure for use in an absorbent article, the laminated structure being defined by a plurality of material layers comprising at least a first layer which is liquid-permeable, a second layer constituting an absorbent core and a third layer, each of said layers being formed of a material having a certain pore radius, said method comprising:
    a first welding step in which said third layer and said second layer are bonded together using ultrasonic welding to create a first welding pattern of bonding sites; and
    a second welding step in which the bonded third and second layers are bonded together with said first layer using ultrasonic welding to create a second welding pattern of bonding sites;
    wherein in the resulting laminated structure of the three layers, the first welding pattern of bonding sites is present only in the second and third layers, and the second welding pattern of bonding sites is present in all three layers, so as to provide a pore gradient extending through the three layers.

2. The method according to according to claim 1, wherein said third layer is a liquid-impermeable backsheet.

3. The method according to claim 1, wherein the absorbent article is a diaper, a sanitary napkin, a panty liner, or an incontinence pad.

4. The method according to claim 1, wherein the pore radius of the first layer is larger than the pore radii of the second and third layers.

5. The method according to claim 1, wherein in the resulting laminated structure, the first layer has fewer bonding sites than the second and third layers.

6. A method for manufacturing a laminated structure for use in an absorbent article, the laminated structure being defined by a plurality of material layers comprising at least a first layer which is liquid-permeable, a second layer constituting an absorbent core and a third layer, each of said layers being formed of a material having a certain pore radius, said method comprising:
    bonding together said material layers by means of at least two ultrasonic welding steps; and
    providing an ultrasonic welding pattern for each of said welding steps, each of said welding patterns being defined by a plurality of bonding sites;
    wherein it comprises:
    providing said welding steps for forming the entire absorbent article;
    selecting said welding patterns in a manner so that the entire laminated structure has a multiple pore radius;
    and wherein said welding steps comprise at least, and in the following sequence:
    a first welding step in which said third layer and said second layer are bonded together; and
    a second welding step in which the bonded third and second layers are bonded together with said first layer;
    wherein said welding steps are carried out using a first layer being formed from a material having a pore radius which is equal to or greater than the pore radius of the second layer and the third layer, and also using a second layer being formed from a material having a pore radius which is equal to or greater than the pore radius of the third layer.

7. An arrangement for manufacturing a laminated structure for use in an absorbent article, the laminated structure including at least a first layer which is liquid-permeable, a second layer constituting an absorbent core and a third layer, each of said layers being formed of a material having a certain pore radius, said arrangement comprising:
    a first ultrasonic welding device arranged for bonding together said second and third material layers, said first ultrasonic welding device constructed so as to impart a first bonding pattern on said second and third material layers;
    a second ultrasonic welding device arranged for bonding together all three material layers, said second ultrasonic welding device constructed so as to impart a second bonding pattern on all three material layers, wherein the second bonding pattern is different than the first bonding pattern;
    wherein said ultrasonic welding devices are arranged so as to provide a pore gradient extending through the three layers.

8. The arrangement to claim 7, wherein the absorbent article is a diaper, a sanitary napkin, a panty liner, or an incontinence pad.

9. A laminated structure for use in an absorbent article, the laminated structure comprising:
    at least a first material layer which is liquid-permeable,
    a second material layer constituting an absorbent core, and
    a third material layer,
    each of said layers being formed of a material having a certain pore radius, said laminated structure being formed by bonding said three material layers together by at least two ultrasonic welding steps providing a different ultrasonic welding pattern for each of said welding steps,
    each of said welding patterns being defined by a plurality of bonding sites wherein the laminated structure is formed through said welding steps; and
    wherein said material layers and welding patterns are selected in a manner so that the entire laminated structure has a graduated pore radius extending through the three layers; and
    said third layer and said second layer are bonded together with a first ultrasonic welding pattern; and the bonded third and second layers are bonded together with said first layer with a second ultrasonic welding pattern.

10. The laminated structure according to claim 9, wherein said third layer is a liquid-impermeable backsheet.

11. The laminated structure according to claim 9, wherein the laminated structure is formed by said welding steps comprising at least, and in the following sequence: a first welding step in which said third layer and said second layer are bonded together; and a second welding step in which the bonded third and second layers are bonded together with said first layer.

12. The laminated structure according to claim 9, wherein said welding steps are carried out using a first layer being formed from a material having a pore radius which is equal to or greater than the pore radius of the second layer and the third layer, and also using a second layer being formed from a material having a pore radius which is equal to or greater than the pore radius of the third layer.

13. The laminated structure according to claim 9, wherein the laminated structure comprises two nonwoven layers and two absorbent cores.

14. The laminated structure according to claim 9, wherein the laminated structure comprises a nonwoven layer, two absorbent cores and a backsheet.

15. The laminated structure to claim 9, wherein the absorbent article is a diaper, a sanitary napkin, a panty liner, or an incontinence pad.

16. An absorbent product comprising a laminated structure according to claim 9.

17. An absorbent product comprising a laminated structure according to claim 10.

18. An absorbent product comprising a laminated structure according to claim 11.

19. An absorbent product comprising a laminated structure according to claim 12.

\* \* \* \* \*